United States Patent [19]

Purdum

[11] 4,385,921

[45] May 31, 1983

[54] CYANOALKYLPHOSPHONATE DIESTERS OF N-PHOSPHONOMETHYLGLYCINONITRILE AS HERBICIDES

[75] Inventor: William R. Purdum, Maryland Heights, Mo.

[73] Assignee: Monsanto Company, St. Louis, Mo.

[21] Appl. No.: 275,484

[22] Filed: Jun. 19, 1981

[51] Int. Cl.³ .................... A01N 57/18; C07F 9/40
[52] U.S. Cl. ................................. 71/86; 260/940
[58] Field of Search ........................ 71/86; 260/940

[56] References Cited

U.S. PATENT DOCUMENTS 4,008,296  2/1977  Barton .................................. 71/86
4,025,331  5/1977  Leber ................................. 260/940

Primary Examiner—Anton H. Sutto
Attorney, Agent, or Firm—Donald W. Peterson; David Bennett; Gordon F. Sieckmann

[57] ABSTRACT

Alkylphosphonate diesters of N-phosphonomethylglycinonitrile are disclosed which are useful as herbicides. This invention further relates to herbicidal compositions containing such alkylphosphonate diesters of N-phosphonomethylglycinonitrile and to herbicidal methods employing such compounds and compositions.

9 Claims, No Drawings

CYANOALKYLPHOSPHONATE DIESTERS OF N-PHOSPHONOMETHYLGLYCINONITRILE AS HERBICIDES

This invention relates to diesters of N-phosphonomethylglycinonitrile which are useful as herbicides. More particularly this invention relates to alkyl phosphonate diesters of N-phosphonomethylglycinonitrile which are useful as herbicides and to herbicidal methods employing such compounds and compositions.

U.S. Pat. No. 4,025,331 issued to Jean-Pierre Leber on May 24, 1977 discloses N-phosphonomethylglycine derivatives of the formula

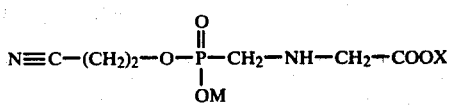

wherein X is hydrogen, unsubstituted or substituted hydrocarbon or a cation and M is hydrogen or a cation. The compounds disclosed in U.S. Pat. No. 4,025,331 supra are said to possess herbicidal and plant growth regulating properties.

The compounds of the present invention are represented by the formula

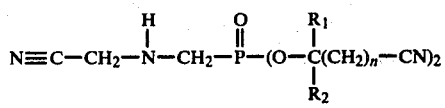

wherein n is an integer 0 or 1.

$R_1$ and $R_2$ are independently hydrogen or lower alkyl.

As employed throughout the claims and description, the term "lower alkyl" includes alkyl radicals which have up to five carbon atoms in a straight or branched chain, for example, methyl, ethyl, propyl, isopropyl, butyl, isobutyl, sec-butyl, t-butyl and pentyl.

In a preferred embodiment, n is preferably 0 or 1.

In accordance with the present invention alkylphosphonate diesters of N-phosphonomethylglycinonitrile of the formula

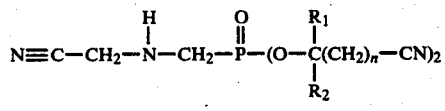

may be prepared by simultaneously reacting a trisubstituted phosphite of the formula

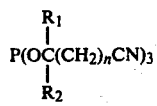

wherein n is as aforedefined with water and with 1,3,5-tri-(cyanomethyl) hexahydro-1,3,5-triazine (trimer of the Schiff's base of formaldehyde and glycinonitrile) of the formula

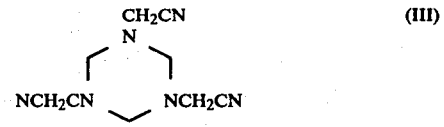

wherein R is as aforedefined to form a crude diester composition containing diester product. A purified diester product may be recovered from the crude diester composition by employing suitable separation means as, for example, employing a chromatographic and/or distillation means having sufficient capability and capacity to effect the aforedescribed recovery.

The aforedescribed reaction is carried out at a temperature in the range from about 10 to 110 and preferably from about 20° to about 90° C.

In preparing diester compounds of formula (I), the range of reactants is not narrowly critical. Preferably, however for each mole of trialkylphosphite employed, one should employ from about 0.5 to about 1.5 mole water, about ¼ to about ½ mole 1,3,5-tricyanomethyl hexahydro-1,3,5-triazine (which is equivalent to 1 mole of the monomer of a Schiff's base of formaldehyde and the corresponding glycinonitrile).

While no catalyst is required for the aforedescribed reaction to proceed a catalyst may be employed if desired.

The reaction time is in the range from about 1 to about 75 and is preferably from about 2 to about 50 hours.

While the process of this invention can be conducted at atmospheric, sub-atmospheric or super-atmospheric pressure, for convenience and economy it is generally preferred to conduct these processes at atmospheric pressure.

Although a suitable solvent may be employed in the aforedescribed process, it is preferred that the reaction be carried out in the absence of a solvent.

Suitable agitation is provided, preferably by stirring or otherwise agitating the reaction composition.

In practicing the aforedescribed process the aforedescribed reactants are admixed together although the reactants may be admixed in any order if desired to form a reaction composition.

The following examples are presented to define the invention more completely without any intention of being limited thereby. All parts and percentages are by weight, unless otherwise specified.

EXAMPLE 1

A reaction composition comprising 15.0 g (0.622 mole) tri-(2-cyanoethyl)phosphite, 1.12 g (0.0622 mole) water and 4.22 (0.0207 mole) of 1,3,5-tri(cyanomethyl)-hexahydro-1,3,5-triazine was agitated at about 25° C. for 12 hours. The resulting product composition was chromatographed on cellulose with ethyl acetate eluent. The product, phosphonic acid, [[(cyanomethyl)amino]methyl],bis (2-cyanoethyl)ester was isolated as a viscous reddish-brown oil in a yield of 7.2 g (45%) and having the following analysis:

Calculated: C, 42.19; H, 5.11; N, 21.87; P, 12.07; Found: C, 42.89; H, 5.23; N, 21.20; P, 11.21.

EXAMPLE 2

A reaction composition comprising of 5 g (0.02 mole) tri-(1-cyanoethyl)phosphite, 0.37 g (0.02 mole) water and 1.4 g (0.0066 mole) of 1,3,5-tri(cyanomethyl)hexahydro-1,3,5-triazine was agitated at about 15° C. for 16 hours. An α-hydroxypropionitrile co-product was removed by bulb to bulb distillation at 30° C. and 0.05 mm Hg. The distillation residue was chromatographed on cellulose (microcrystalline) with eluent of ethyl acetate:cyclohexane (1:3). The collected column concentrates were placed in vacuo at 60° C. (0.1 mmHg) for 30 minutes with the residue being the desired product. The product, phosphonic acid, [[(cyanomethyl)amino]methyl],bis (1-cyanoethyl)ester was obtained as a viscous reddish-colored oil in a yield of 1.4 g (27%) and having the following analysis:

Calculated: C, 42.19; H, 5.11; N, 21.87; P, 12.09;
Found: C, 42.14; H, 5.38; N, 20.45; P, 11.40.

EXAMPLE 3

The post-emergent herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergent herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | | | |
| --- | --- | --- | --- |
| A — | Canada Thistle* | K — | Barnyardgrass |
| B — | Cocklebur | L — | Soybean |
| C — | Velvetleaf | M — | Sugar Beet |
| D — | Morningglory | N — | Wheat |
| E — | Lambsquarters | O — | Rice |
| F — | Smartweed | P — | Sorghum |
| G — | Yellow Nutsedge* | Q — | Wild Buckwheat |
| H — | Quackgrass* | R — | Hemp Sesbania |
| I — | Johnsongrass* | S — | Panicum Spp |
| J — | Downey Brome | T — | Crabgrass |

*Established from vegetative propagules.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 4 | 11.2 | 2 | 1 | 0 | 2 | 1 | 1 | 1 | 1 | 0 | 0 | 1 |
|  | 2 | 5.6 | 0 | 0 | 0 | 0 | 1 | 0 | 0 | 0 | 0 | 0 | 0 |
| 2 | 4 | 11.2 | 2 | 2 | 2 | 2 | 2 | 4 | 3 | 2 | 3 | 1 | 3 |
|  | 4 | 5.6 | 2 | 2 | 2 | 2 | 3 | 4 | 3 | 1 | 4 | 2 | 2 |

TABLE II

| Compound of Example No. | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| 2 | 4 | 5.6 | 1 | 1 | 2 | 2 | 4 | 3 | 0 | — | 0 | 4 | 2 | 2 | 3 | 1 | 3 | 2 |
|  | 4 | 1.12 | 1 | 0 | 0 | 0 | 3 | 1 | 1 | 1 | 0 | 2 | 0 | 1 | 0 | 0 | 1 | 2 |
|  | 2 | 0.28 | 0 | 0 | 0 | 0 | 1 | 0 | 0 | 0 | 0 | 1 | 0 | 0 | 0 | 0 | 0 | 0 |

— indicates species of plant absent during test.

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent," it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

|   |   |   |
|---|---|---|
| 1. | Phosphonic Acid, [[(cyanomethyl)-amino]methyl]-, Bis(2-cyanoethyl) ester | 95 parts |
|    | Methanol | 5 parts |
| 2. | Phosphonic Acid, [[(cyanomethyl)-amino]methyl]-, Bis(1-cyanoethyl) ester | 95 parts |
|    | Ethoxylated nonyl phenol | 5 parts |
| 3. | Phosphonic Acid, [[(cyanomethyl)-amino]methyl]-, Bis(1-cyanoethyl) ester | 90 parts |
|    | Isopropanol | 10 parts |
| 4. | Phosphonic Acid, [[(cyanomethyl)-amino]methyl]-, Bis(2-cyanoethyl) ester | 90 parts |
|    | Ethoxylated octyl phenol | 10 parts |
| 5. | Phosphonic Acid, [[(cyanomethyl)-amino]methyl]-, Bis(1-cyanoethyl) ester | 90 parts |
|    | Chloroform | 5 parts |
|    | Ethoxylated dinonyl phenol | 5 parts |
| 6. | Phosphonic Acid, [[(cyanomethyl)-amino]methyl]-, Bis(2-cyanoethyl) ester | 75 parts |
|    | Acetonitrile | 25 parts |
| 7. | Phosphonic Acid, [[(cyanomethyl)-amino]methyl]-, Bis(1-cyanoethyl) ester | 75 parts |
|    | Ethoxylated oleyl alcohol | 25 parts |
| 8. | Phosphonic Acid, [[(cyanomethyl)-amino]methyl]-, Bis(2-cyanoethyl) ester | 75 parts |
|    | Acetonitrile | 15 parts |
|    | Ethoxylated cocoamine | 10 parts |
| 9. | Phosphonic Acid, [[(cyanomethyl)-amino]methyl]-, Bis(1-cyanoethyl) ester | 75 parts |
|    | 1,2-Dimethoxyethane | 20 parts |
|    | Ethoxylated tallow amine | 5 parts |
| 10. | Phosphonic Acid, [[(cyanomethyl)-amino]methyl]-, Bis(1-cyanoethyl) ester | 50 parts |
|    | Dimethylformamide | 50 parts |
| 11. | Phosphonic Acid, [[(cyanomethyl)-amino]methyl]-, Bis(2-cyanoethyl) ester | 50 parts |
|    | Isopropyl dodecylbenzene sulfonate | 50 parts |
| 12. | Phosphonic Acid, [[(cyanomethyl)-amino]methyl]-, Bis(2-cyanoethyl) ester | 50 parts |
|    | Dimethylsulfoxide | 40 parts |
|    | Ethoxylated soybeanamine | 10 parts |
| 13. | Phosphonic Acid, [[(cyanomethyl)-amino]methyl]-, Bis(2-cyanoethyl) ester | 50 parts |
|    | α-butyrolactone | 25 parts |
|    | Triethanolamine dodecylbenzene sulfonate | 25 parts |
| 14. | Phosphonic Acid, [[(cyanomethyl)-amino]methyl]-, Bis(1-cyanoethyl) ester | 50 parts |
|    | 1,1,1-Trichloroethane | 42 parts |
|    | Ethoxylated nonyl phenol | 8 parts |
| 15. | Phosphonic Acid, [[(cyanomethyl)-amino]methyl]-, Bis(1-cyanoethyl) ester | 25 parts |
|    | Chloroform | 75 parts |
| 16. | Phosphonic Acid, [[(cyanomethyl)-amino]methyl]-, Bis(1-cyanoethyl) ester | 25 parts |
|    | Chloroform | 70 parts |
|    | Ethoxylated tallow amine | 5 parts |
| 17. | Phosphonic Acid, [[(cyanomethyl)-amino]methyl]-, Bis(1-cyanoethyl) ester | 25 parts |
|    | 1,1,1-Trichloroethane | 74 parts |
|    | Ethoxylated oleyl alcohol | 1 part |
| 18. | Phosphonic Acid, [[(cyanomethyl)-amino]methyl]-, Bis(1-cyanoethyl) ester | 25 parts |
|    | Chloroform | 68 parts |
|    | Ethoxylated dinonyl phenol | 7 parts |
| 19. | Phosphonic Acid, [[(cyanomethyl)-amino]methyl]-, Bis(1-cyanoethyl) ester | 10 parts |
|    | Chloroform | 90 parts |
| 20. | Phosphonic Acid, [[(cyanomethyl)-amino]methyl]-, Bis(2-cyanoethyl) ester | 10 parts |
|    | Methanol | 80 parts |
|    | Polyoxypropylene - polyoxyethylene block copolymer | 10 parts |
| 21. | Phosphonic Acid, [[(cyanomethyl)-amino]methyl]-, Bis(1-cyanoethyl) ester | 10 parts |
|    | Ethanol | 88 parts |
|    | Polyoxyethylene (20) sorbitan-monolaurate | 2 parts |
| 22. | Phosphonic Acid, [[(cyanomethyl)-amino]methyl]-, Bis(1-cyanoethyl) ester | 10 parts |
|    | Isopropanol | 72 parts |
|    | Polyoxyethylene sorbitan-monooleate | 18 parts |
| 23. | Phosphonic Acid, [[(cyanomethyl)-amino]methyl]-, Bis(2-cyanoethyl) ester | 5 parts |
|    | Dimethylformamide | 95 parts |
| 24. | Phosphonic Acid, [[(cyanomethyl)-amino]methyl]-, Bis(1-cyanoethyl) | 5 parts |

| | |
|---|---|
| ester | |
| Acetonitrile | 90 parts |
| Ethoxylated tallow amine | 5 parts |
| 25. Phosphonic Acid, [[(cyanomethyl)-amino]methyl]-, Bis(1-cyanoethyl) ester | 5 parts |
| Ethanol | 94 parts |
| Ethoxylated tallow amine | 1 part |
| 26. Phosphonic Acid, [[(cyanomethyl)-amino]methyl]-, Bis(2-cyanoethyl) ester | 5 parts |
| Isopropanol | 80 parts |
| Ethoxylated cocoamine | 15 parts |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It it believed that one skilled in the art can readily determine from the teachings of this specification, including examples, the approximate application rate.

There are several methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another application method, shielded applicators may be employed to direct the liquid composition in the form of a spray onto the weeds while effectively shielding the crops from the spray.

These and other application methods for selectively applying liquid compositions to weeds are discussed in detail in Innovative Methods of Post-Emergence Weed Control, McWhorter C. G., Southern Weed Science Society, 33rd Annual Meeting Proceedings, Jan. 15–17, 1980; Auburn University Printing Service, Auburn, Ala., U.S.A., the teachings of which are incorporated herein by reference in their entirety.

Another method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

The aforementioned and other methods for applying liquid compositions to plants are discussed in detail in "Rope Wick Applicator—Tool With A Future," Dale, James E., pp. 3–4, "The Recirculating Sprayer and Roundup ® Herbicide," Derting, Claude W., pp. 5–7, and "C.D.A. Herbicide Application," McGarvey, Frank X., *Weeds Today*, Volume 11, Number 2, pp. 8–9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound useful as a herbicide of the formula

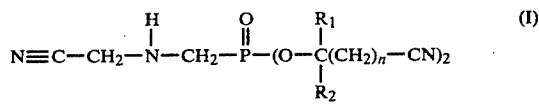

wherein n is an integer 0 or 1, and $R_1$ and $R_2$ are independently hydrogen or lower alkyl.

2. A compound of claim 1 wherein n is 0.

3. A compound of claim 1 wherein n is 1.

4. A herbicidal composition comprising a herbicidally effective amount of a compound of claim 1, together with an inert diluent.

5. A herbicidal composition comprising a herbicidally effective amount of a compound of claim 2, together with an inert diluent.

6. A herbicidal composition comprising a herbicidally effective amount of a compound of claim 3, together with an inert diluent.

7. A herbicidal method which comprises contacting a plant with a herbicidally effective amount of a compound of claim 1.

8. A herbicidal method which comprises contacting a plant with a herbicidally effective amount of a compound of claim 2.

9. A herbicidal method which comprises contacting a plant with a herbicidally effective amount of a compound of claim 3.

* * * * *